(12) United States Patent
Remer

(10) Patent No.: US 8,026,389 B2
(45) Date of Patent: Sep. 27, 2011

(54) SOLID AND WATER-SOLUBLE ACTIVE INGREDIENT AND HERBICIDE FORMULATION, PRODUCTION PROCESS THEREFOR, AND PROCESS FOR CONTROLLING WEEDS

(76) Inventor: Ricardo Amaral Remer, Rio de Janeiro (BR)

( * ) Notice: Subject to any disclaimer, the term of this patent is extended or adjusted under 35 U.S.C. 154(b) by 336 days.

(21) Appl. No.: 12/520,341

(22) PCT Filed: Dec. 17, 2007

(86) PCT No.: PCT/BR2007/000343
§ 371 (c)(1),
(2), (4) Date: Jun. 19, 2009

(87) PCT Pub. No.: WO2008/070947
PCT Pub. Date: Jun. 19, 2008

(65) Prior Publication Data
US 2010/0144528 A1      Jun. 10, 2010

(30) Foreign Application Priority Data

Dec. 15, 2006  (BR) .................................... 10605346
May 16, 2007  (BR) .................................... 10702599

(51) Int. Cl.
*C07F 9/22*      (2006.01)
(52) U.S. Cl. ......................................................... 562/17
(58) Field of Classification Search ..................... 562/17
See application file for complete search history.

(56) References Cited

U.S. PATENT DOCUMENTS
7,683,207 B2 *   3/2010   Tai et al. ........................ 562/11
* cited by examiner

*Primary Examiner* — Peter O Sullivan
(74) *Attorney, Agent, or Firm* — Laurence P. Colton; Smith Risley Tempel Santos LLC

(57) ABSTRACT

The present invention provides active ingredients and herbicide formulations, as well as the production processes therefor. The active ingredient of the invention is a dry, solid ammonium salt of glyphosate, having high purity (95 to 100%) and low humidity (<1.0% m/m), and is useful as "technical salt" for the preparation of dry, solid, and water-soluble herbicide formulations of the invention. The production process of said active ingredient comprises a solid/liquid/solid reaction between a solid ammonium salt and solid glyphosate acid, both solid being dispersed in an organic liquid medium. The products of the invention are highly water-soluble and are useful for controlling crop weeds.

17 Claims, 4 Drawing Sheets

SOLID AND WATER-SOLUBLE ACTIVE INGREDIENT AND HERBICIDE FORMULATION, PRODUCTION PROCESS THEREFOR, AND PROCESS FOR CONTROLLING WEEDS

FIELD OF THE INVENTION

The present invention is related to agrochemicals and production processes therefore. More specifically, the present invention discloses a process for the production of a solid ammonium salt of n-phosphonomethyl glycine ([$HOOCH_2NHCH_2PO(OH)_2$].$NH_3$, generally known as ammonium salt of glyphosate, in high purity (95 to 100%) and low humidity (<1.0% m/m), as an active ingredient of solid, and water-soluble herbicide formulation. The production process of said active ingredient comprises a solid/liquid/solid reaction between a solid ammonium salt and solid glyphosate acid, both solid being dispersed in an organic liquid medium. The thus obtained ammonium salt of glyphosate has low or zero solubility in the liquid medium, therefore precipitating in said liquid medium and thus allowing its separation in the form of a highly pure and concentrated solid. The product of such reaction scheme is highly water-soluble and can be used directly for controlling crop weeds and/or as active ingredient for the preparation of agrochemical formulations containing the ammonium salt of glyphosate. The preferred herbicide formulations of the invention comprise said active ingredient and are also solid and water-soluble.

RELATED PRIOR ART

Patent prior art relating to the subject-matter of the invention is vast. However, none of the documents found in the art anticipates or indisputably suggests the teachings of the invention, nor the skilled person in the art would reach the invention or be motivated to combine any of such documents so as achieve the teachings herein provided.

Glyphosate (n-phosphonomethylglycine) is known in the art as an effective herbicide. Glyphosate is a poorly water-soluble organic acid, and is typically commercialized in liquid or past form, or, when in its water-soluble salt forms such as the isopropylamine salt, in formulations comprising it. Several glyphosate salts, formulations, and production processes therefore are available in the art. Examples include: Patents U.S. Pat. Nos. 3,799,758; 4,405,531; 4,315,765; 4,507,250; 4,397,676; 4,481,026; 4,140,513; Brazilian Patent PI 7201355, U.S. Pat. No. 6,475,954, European Patent EP 568635, WO 9325081, WO 9007275, U.S. Pat. Nos. 6,228,807, 5,656,572, European Patent EP 0321527, U.S. Pat. No. 6,468,944, Brazilian Patent Applications PI 0101302, PI 9810811, PI 9306732, and PI 9915566, WO 9702742, European Patent EP 0448538, U.S. Pat. No. 6,274,156, European Patent EP 0853883, and U.S. Pat. No. 5,994,269.

The most related prior art include the Brazilian Patent Application PI 0013186, of Monsanto Company and entitled "Processo para obtenção de uma pasta de glifosato de amônio processável a jusante". Such document discloses a process for the obtainment of ammonium salts of glyphosate. The process consists of admixing ingredients so as to obtain a paste which is then submitted to an extrusion process. The essential steps of said process include the preparation of a downstream processable paste by admixing:

(i) particulated acid glyphosate;
 (ii) ammonia in a proportion of about 0.8 to about 1.25 mol by mol of acid glyphosate; and
 (iii) water, in a proportion of about 10% to about 25% in weight of all materials being admixed, thus causing the reaction of acid glyphosate with ammonia. The reaction is exotermic and the generated heat provokes partial evaporation of water so as to form an ammonium glyphosate salt having about 5% to 20% of humidity. In said document, the ammonium source may be aqueous or anhydrous ammonia, the latter being in liquid or gaseous form.

Brazilian Patent Application PI 0312663, filed by Chinese inventors, is entitled "Preparação de Glifosato de Amônio Sólido Usando Solvente Orgânico em Extração". Such document discloses a process for the preparation of the ammonium salt of glyphosate by means of organic solvent extraction in a gas/liquid/solid reaction scheme. Such process consists in adding acid glyphosate and water in a reactor having homogenizing means; introducing gaseous ammonia to the reactor so as acid glyphosate reacts therewith and a solution of the ammonium salt of glyphosate is formed by the end of the reaction; adding a water-soluble organic solvent such as methanol or ethanol or formaldehyde so as to decrease the solubility of the ammonium salt of glyphosate in the system, thereby crystallizing it; and suction-filtering it, optionally drying it so as to obtain a solid.

The Brazilian Patent Application PI 9205234-7 (equivalent to U.S. Pat. No. 5,324,708), was filed by Alkaloida Vegyeszeti Gyar and is entitled "Novos Sais de Mono-amônio Não-higroscópicos". This application was rejected and discloses monoisopropylamine salts of gluphosinate or glyphosate, as well as processes for the production thereof. Herbicides and methods for controlling weeds are described and claimed, but no process is claimed. Said processes consist in the reaction of the corresponding phosphinic or phosphonic acid, in solid form, in a reactor containing liquid monoisopropylamine salt, also known as MIPA. The reaction is therefore a solid/liquid/liquid reaction scheme. Several disadvantages of said processes and of the corresponding products occur, and include: the products are glufosinate or glyphosate MIPA salts, whose dissolutions in water are highly exothermic, posing risks and difficulties to the final user. Also, the use of MIPA in an industrial plant is highly dangerous: beyond being highly toxic (MIPA is considered as IDLH immediately dangerous to Life and Health), MIPA is also flammable. The reaction between MIPA the phosphinic or phosphonic acid is also exotermic, thus requiring sophisticated reaction controls in the industrial processing and the corresponding costs.

The present invention provides, between other advantages, a new solid dry and water-soluble active ingredient and agrochemical formulations containing the ammonium salt of glyphosate. The active ingredient of the invention is heretofore referred to as "technical monoammonium salt of glyphosate", or simply "technical salt", which has a purity of at least 95%, preferably 95.5%. The solid dry formulation provides several advantages such as transportation economy and, most importantly, substantial reduction in the capital and operating costs of the corresponding industrial plant, as compared to other known technologies for producing water-dispersible granules containing glyphosate. These and other advantages of the invention will be appreciated by the skilled persons.

In short, no document was found in the art specifically disclosing a process for producing the ammonium salt of glyphosate in a solid/liquid/solid reaction scheme between a solid ammonium salt and solid acid glyphosate, these solids being dispersed in an organic liquid medium. The present invention enables the obtainment of the ammonium salt of glyphosate, which is insoluble in the reaction medium and thus allows its direct isolation in the form a highly pure and concentrated salt. Further, the equipments required for the process of the present invention are much more simple and cheaper than those of similar processes known in the art. The process of the invention also avoids using gaseous or liquid anhydrous ammonia as ammonium cation source, therefore eliminating the corresponding concerns regarding safety and environmental issues. These and other disadvantages of the processes known in the art are overcome by the process and products of the present invention.

SUMMARY OF THE INVENTION

One of the objects of the present invention is to provide an improved process for producing the ammonium salt of glyphosate in solid form. The product of such process is another object of the invention, and is useful as herbicide active ingredient of agrochemical formulations, which in turn can be available in several forms such as combinations with other herbicides, insecticides, fungicides and other pest control formulations.

It is another object of the invention to provide a production process which requires less capital and operational costs for producing the ammonium salt of glyphosate.

It is another object of the invention to provide a safer production process, since the process of the invention does not require the use of toxic or dangerous consumables such as those of the processes known in the art.

It is another object of the invention to provide a more environmental-friendly production process, since the process of the invention does nor require the use of toxic or dangerous consumables such as those of the known process in the art, and most of the reagents are reused and/or recycled during the process without producing large amount of industrial waste.

In another feature of the invention, being therefore another of its objects, the conditions of the process for obtaining the ammonium salt of glyphosate circumvent the technical problem of heat generation, as occurs with the processes known in the art.

In another feature of the invention, being therefore another of its objects, the active ingredient which is a product of the invention is a highly pure and concentrated ammonium salt of glyphosate in the solid form, which is in contrast to the processes known in the art.

In another feature of the invention, being therefore another of its objects, the active ingredient which is a product of the invention has low water content, thus substantially reducing the technical problems and costs for manipulation and transport, which is in contrast to the processes known in the art.

Another object of the present invention is to provide an improved process for preparing dry, solid and water-soluble herbicide formulations comprising the ammonium salt of glyphosate.

Another object of the present invention is to provide highly pure and improved herbicide formulations in the form of a water-soluble powder, which is in contrast to the related products known in the art.

Another object of the present invention is to provide highly pure and improved herbicide formulations in the form of water-soluble granules, which is in contrast to the related products known in the art.

Another object of the present invention is to provide highly pure and improved herbicide formulations in the form of water-dispersible granules, which is in contrast to the more costly related products known in the art.

These and other objects of the invention will be readily appreciated by the skilled persons and by the industries in this technical field. Further details are heretofore provided so as such skilled persons can reproduce the invention.

DETAILED DESCRIPTION OF THE INVENTION

Figure 1:
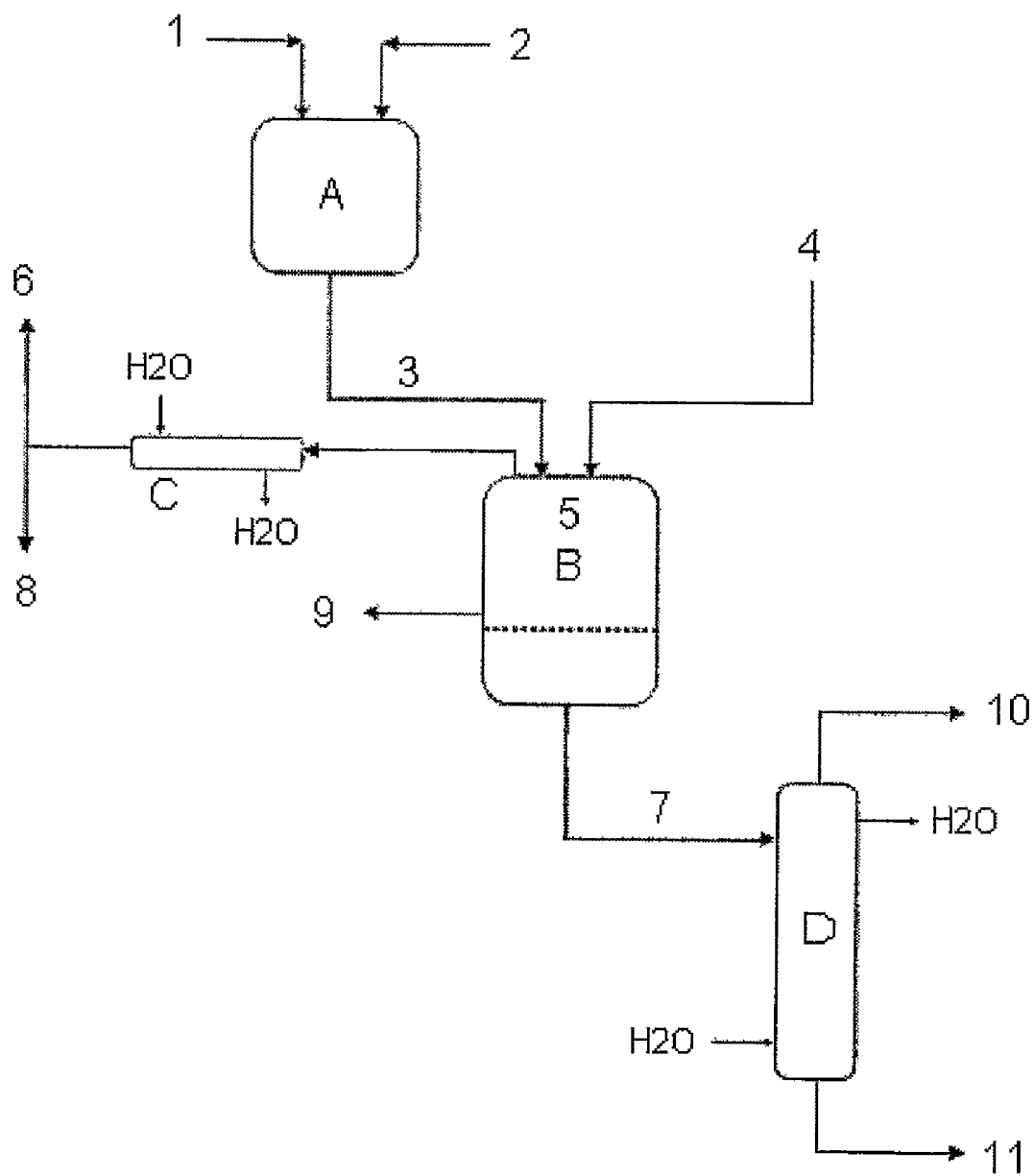
FIG. 1 shows a schematic diagram of a preferred embodiment an industrial scale process for producing the solid, dry and water-soluble ammonium salt of glyphosate (the "technical salt"), where: an agitated stainless steel tank (A); an agitated stainless steel reactor (B) comprising a dryer and filter; a condenser (C); a recovery column (D); and the materials flow lines (1), (2), (3), (4), (5), (6), (7), (8), (9), (10) and (11).

The inventor, searching for alternative technical solutions for the problems of the products and processes known in the art, developed an improved process for producing the ammonium salt of glyphosate in the form of a highly pure and concentrated solid.

In the present invention, all concentrations are indicated in % weight/weight, except when specified in the contrary. The ammonium salt of glyphosate is obtained in the present invention by the reaction between a solid acid glyphosate (for example, in the form of humid or dry cake, the latter being preferred) and solid, water-insoluble ammonium salts, said solids reacting in a liquid organic medium consisting, under room temperature (the reaction is not exotermic) and with constant agitation until the reaction is complete. The reaction therefore occurs in a solid/liquid/solid system. The thus obtained ammonium salt of glyphosate is not soluble in the organic liquid medium and therefore precipitates, thus allowing its easy isolation with high purity and concentration. The product of the reaction, although being insoluble in the organic liquid medium, is sufficiently water soluble so as to be directly used as agrochemical and/or used as active ingredient for the preparation of herbicide formulations containing the ammonium salt of glyphosate. The thus obtained product (the ammonium salt of glyphosate) is then isolated and optionally dried by classical methods. The remaining liquid can be recycled for the next batch without any previous treatment preferably up to about five cycles and then recovered by simple destilation. The ammonium salts used in the process of the present invention are, preferably, ammonium hydrogen carbonate and/or ammonium carbonate. The organic liquid medium is a solvent in which the final product has low or no solubility, being preferred in the invention alcohols of up to four carbon atoms. The most preferred solvent is ethanol, for its low cost, low toxicity and high availability. The following examples illustrate, but are not intended to limit, some forms of reducing the invention to practice.

Example 1

In a mechanically agitated reactor, 810.0 g of commercial ethanol (96%) and 356.0 g of solid acid glyphosate 95.5% (2.00 moles) were fed. Subsequently, 100.8 g of ammonium carbonate (1.05 moles) were fed and the mixture was agitated under room temperature for about 30 minutes, so as the reaction completes. The reaction can be simplified as follows:

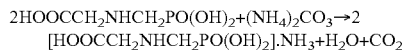
$2HOOCCH_2NHCH_2PO(OH)_2+(NH_4)_2CO_3 \rightarrow 2[HOOCCH_2NHCH_2PO(OH)_2].NH_3+H_2O+CO_2$ The contents of the reactor were filtered and the solids dried until constant weight. The remaining liquid (licquor) was reused for the next batch. The process yielded 386.8 g of the ammonium salt of glyphosate, having <1.0% w/w humidity and >95.5% purity.

Example 2

In a mechanically agitated reactor, 810.0 g of commercial ethanol (96%) and 395.6 g of humid cake acid glyphosate 85.5% (2.00 moles) were fed. Subsequently, 100.8 g of ammonium carbonate (1.05 moles) were fed and the mixture was agitated under room temperature for about 30 minutes, so as the reaction completes. The contents of the reactor were filtered and the solids dried until constant weight. The remaining liquid (licquor) was reused for the next batch. The process yielded 385.3 g of the ammonium salt of glyphosate, having <1.0% w/w humidity and >95.5% purity.

Example 3

The conditions of example 1 were repeated now using 810.0 g of methanol 98%. The process yielded 385.5 g of the ammonium salt of glyphosate, having <1.0% w/w humidity and >95.5% purity. The results are similar to those using ethanol, but since methanol is knowingly toxic, this raised enhanced concerns regarding occupational health.

Example 4

The conditions of example 1 were repeated now using 162.0 g of ammonium hydrogen carbonate (2.05 moles). The process yielded 385.2 g of the ammonium salt of glyphosate, having <1.0% w/w humidity and >95.5% purity. The results are similar to those using ammonium carbonate, but in this case a higher specific consumption occurred because of the altered stechiometric relation.

Example 5

The conditions of example 3 were repeated now using 162.0 g of ammonium hydrogen carbonate (2.05 moles). The process yielded 385.5 g of the ammonium salt of glyphosate, having <1.0% w/w humidity and >95.5% purity. The results are similar to those using ammonium carbonate.

Example 6

The process of the present invention was also tested in industrial scale. Making reference to FIG. 1: the line (1) feeds tank (A) with commercial ethanol (96%), while line (2) feeds solid acid glyphosate 95.5% to tank (A), which is kept agitated for homogeneity. Subsequently, line (3) feeds the contents of tank (A) to reactor (B), which is also fed by line (4) with ammonium carbonate. The mixture is homogenized under room temperature for about 30 minutes until the reaction is complete. The reaction occurring in reactor (B) can be described as follows:

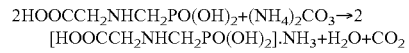
$2HOOCCH_2NHCH_2PO(OH)_2+(NH_4)_2CO_3 \rightarrow 2[HOOCCH_2NHCH_2PO(OH)_2].NH_3+H_2O+CO_2$ The contents of reactor (B) is then filtered, and the resulting liquid (licquor) containing alcohol is directly reused for the next batch or optionally fed by line (7) to a recovery column (D). The final product, the solid ammonium salt of glyphosate, is obtained in line (9) and, after drying until constant weight, has <1.0% w/w humidity and >95.5% purity. The yield of this preferred embodiment of the invention is >98%. It is worth noting, making reference to FIG. 1, that the production plant is quite simple and does not require utilities such as vapor, cold water etc. The use of $N_2$ for the control of the atmosphere within the tank and reactor is recommended in some cases (compliance to Brazilian rules). The gases formed in reactor (B) are preferably treated in a condenser (C). The solvent recovery for reuse is quite simple for any plant having heat sources such as vapor.

Table 1 shows a mass balance for the production plant of the "technical salt" of the present example, where all lines of FIG. 1 are again shown, together with the corresponding product and flow/mass.

TABLE 1

Schematic mass balance of an industrial plant operating a preferred embodiment of the invention.

| Product | Line 1 | 2 | 3 | 4 | 5 | 6 | 7 | 8 | 9 | 10 | 11 |
|---|---|---|---|---|---|---|---|---|---|---|---|
| Alcool | | 778 | | 778 | | 778 | | 661 | 117 | 778 | |
| Carbonate | 96 | | | | 100.0 | | | | | | |
| Amonia | | | | | | | | | | | |
| Acid | 169.1 | | 336 | 336 | | | | | | | |
| Glifosate 95% | | | | | | | | | | | |
| $H_2O$ | 18 | 32 | | 32 | | 50 | | 43 | 8 | 32 | 18 |
| Salt | 186.1 | | | | | 369 | | | 369 | | |
| Glifosate | | | | | | | | | | | |
| $CO_2$ | 44 | | | | | 46 | 45.9 | | | | |
| Others | | | 18 | 18 | | 17 | | | 18 | | |
| Total | | 810 | 353 | 1163 | 100 | 1260 | 46 | 704 | 124 | 387.71 | 810 | 18 |

Obs.: in the present example ammonium carbonate is used, but ammonium hydrogen carbonate can also be used upon the corresponding adaptations.

The "technical salt" obtained in the present invention is an active ingredient that can be used in several ways and formulations, including those combining this active with other actives such as other herbicides, fungicides etc. The inventor also developed new and improved herbicide formulations containing the "technical salt" of the invention, said herbicide formulations also being dry, solid and water soluble, as well as developed processes for preparing said herbicide formulations. The herbicide formulations of the invention comprise the "technical salt" of the invention and at least one dry, solid adjuvant, optionally further comprising inert compounds. The preferred adjuvants of the invention comprise powdered etoxylated C16-C18 alcohols, the preferred inert compound being ammonium sulphate. The herbicide formulations of the invention may also optionally comprise stabilizers, the preferred stabilizer being sodium sulphide.

As regards performance, the herbicide formulations of the invention are equivalent to those available in the market, such as: MIPA salts (in the form of water solution); diammonium salts in the form of water solution; and WDG salts. The dry, solid surfactants that can be used in the present invention are commercially available, the preferred being selected from powdered etoxylated C16-C18 alcohols. The skilled in the art of formulating herbicides will appreciate from the present teachings that other surfactants or combinations thereof may also be used, provided that achieving the corresponding technical requirements, that is, to provide enhanced contact of the active ingredient with the plant surface and/or enhance penetration in the plant. The preferred formulations of the invention comprise 720 g/kg, in terms of acid glyphosate, corresponding to 792.4 g/kg in terms of the "technical salt" or monoammonium salt of glyphosate. The massic proportion of the preferred formulations of the invention are described in table 2.

TABLE 2

| Ingredients: | % w/w |
|---|---|
| Monoammonium salt of Glyphosate | 80.8 |
| Surfactants | 10.1 |
| Inert(s) | 8.7 |
| Stabilizer(s) | 0.4 |

The monoammonium salt of glyphosate or "technical salt" used in the herbicide formulations of the invention preferably has <1% w/w. The herbicide formulations of the invention may also comprise other additives such as thickers, antifoaming agents, umectants, colorants, dispersants and combinations thereof.

The herbicide formulations of the invention can be easily dissolved in water by the final user before use. The proper usage of the active ingredient will depend of the plant species to be controlled. Typically the usage is of about 90 to 360 g of glyphosate per hectare, as calculated in terms of acid glyphosate.

In the following examples several processes for the preparation of dry, solid herbicide formulations are provided, all comprising the high purity "technical salt" of the invention.

Example 7

In a preferred embodiment of the invention, it is provided an industrial scale process for producing solid, dry and water-soluble herbicide formulations in the form of powder comprising the ammonium salt of glyphosate. Note that herbicide formulations in the form of powder comprising the ammonium salt of glyphosate are nor known in the art. Making reference to FIG. 2: two parallel Ribbon Blenders, in which the dry, solid "technical salt" and an dry, solid adjuvant, preferably powdered C16-C18 etoxylated alcohols, are homogenized; the mixture leaving said Ribbon Blenders (1 and/or 2) is fed to a Jet Mill and subsequently to a filter. The solid material leaving said filter is fed to the Ribbon Blender 3, to which sodium sulphide and/or ammonium sulphate is/are also fed. The moisture leaving Ribbon Blender 3 is a dry, solid and water-soluble herbicide formulation comprising the ammonium salt of glyphosate at a concentration of 720 g/kg (% in weight based on the acid glyphosate). Such formulation is then submitted to a packaging unit.

Example 8

Figure 2:
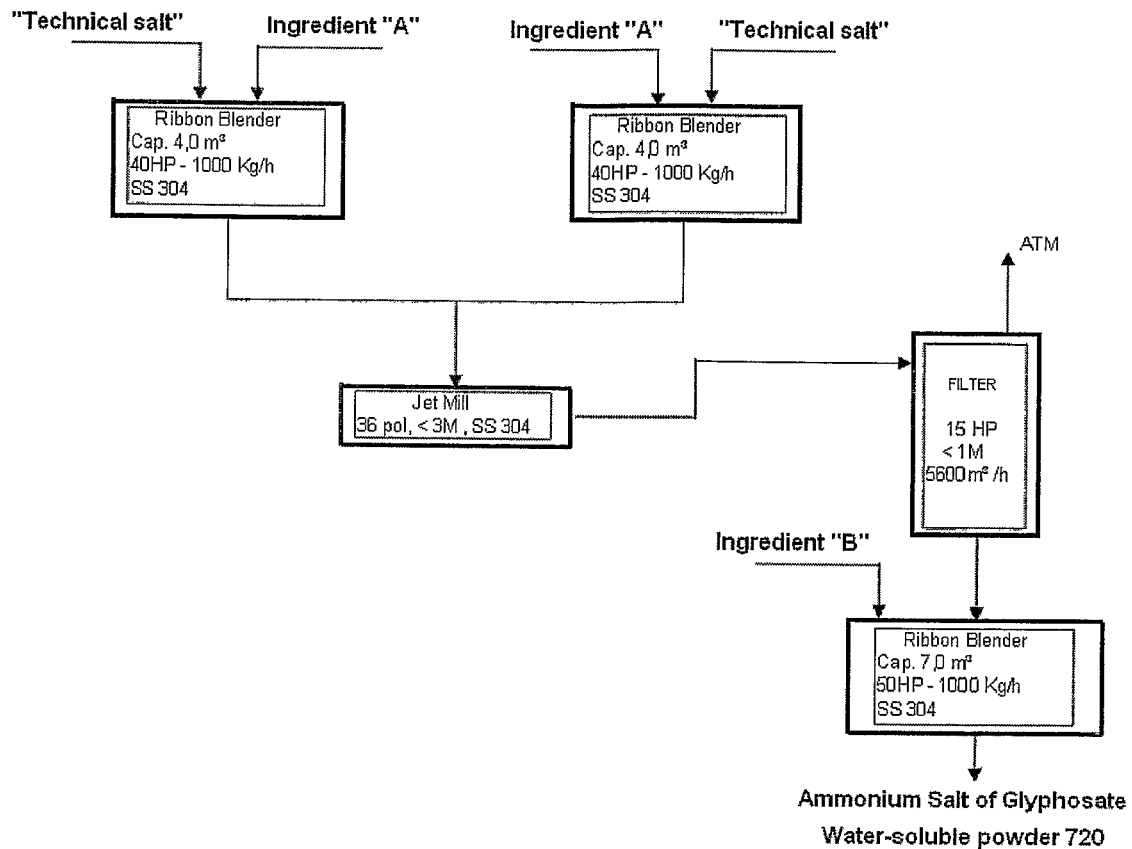
FIG. 2 shows a schematic diagram of a preferred embodiment of an industrial scale process for producing the solid, dry and water-soluble herbicide formulations in the form of powder comprising the ammonium salt of glyphosate, where: two parallel Ribbon Blenders, in which the technical salt and an ingredient "A" are homogenized; the mixture leaving said Ribbon Blenders (1 and/or 2) is fed to a Jet Mill and subsequently to a filter. The solid material leaving said filter is fed to the Ribbon Blender 3, to which an ingredient "B" is also fed. The moisture leaving Ribbon Blender 3 is a dry, solid and water-soluble herbicide formulation comprising the ammonium salt of glyphosate at a concentration of 720 g/kg (in weight based on the acid glyphosate). Such formulation is then submitted to a packaging unit.
Figure 3:
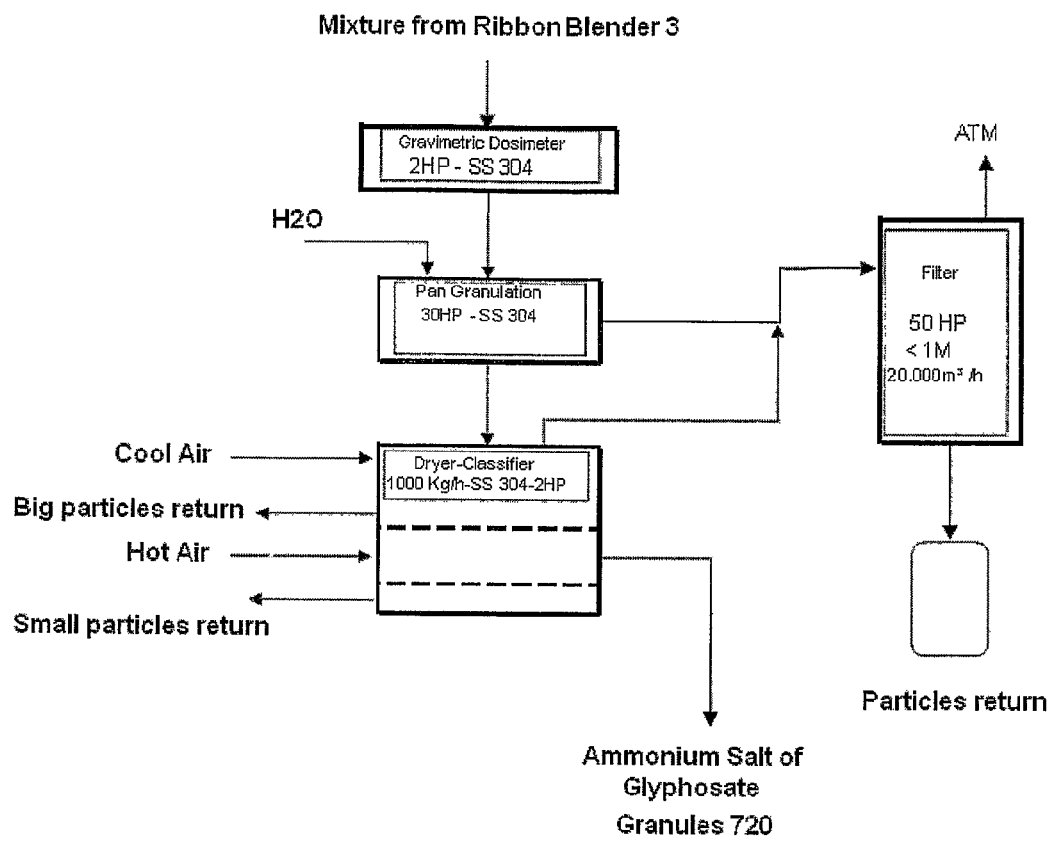
FIG. 3 shows a schematic diagram of another preferred embodiment of an industrial scale process for producing the solid, dry and water-soluble herbicide formulations in the form of granules comprising the ammonium salt of glyphosate, where: the mixture leaving Ribbon Blender 3 shown in FIG. 2 is fed to a gravimetric dosimeter and then to a Pan Granulator, to which water is also fed; solid spheres of the formulation are formed in the Pan Granulator, and said material is then fed to a Dryer-Classifier; the solid residues formed in the Pan Granulator and in the Dryer-Classifier are fed to a filter, so as said solid material is recycled; the dry, solid spheres of the formulation which are within the specifications leave the Dryer-Classifier as a formulation comprising the ammonium salt of glyphosate in the form of water-soluble granules having a concentration of about 720 g/kg (based on the weight of acid).

In another preferred embodiment of the invention, it is provided an industrial scale process for producing the solid, dry and water-soluble herbicide formulations in the form of granules comprising the ammonium salt of glyphosate. Making reference to FIG. 3: the mixture leaving Ribbon Blender 3 shown in FIG. 2 is fed to a gravimetric dosimeter and then to a Pan Granulator, to which water is also fed; solid spheres of the formulation are formed in the Pan Granulator, and said material is then fed to a Dryer-Classifier; the solid residues formed in the Pan Granulator and in the Dryer-Classifier are fed to a filter, so as said solid material is recycled; the dry, solid spheres of the formulation which are within the specifications leave the Dryer-Classifier as a formulation comprising the ammonium salt of glyphosate in the form of water-soluble granules having a concentration of about 720 g/kg (based on the weight of acid).

Example 9

Figure 4:
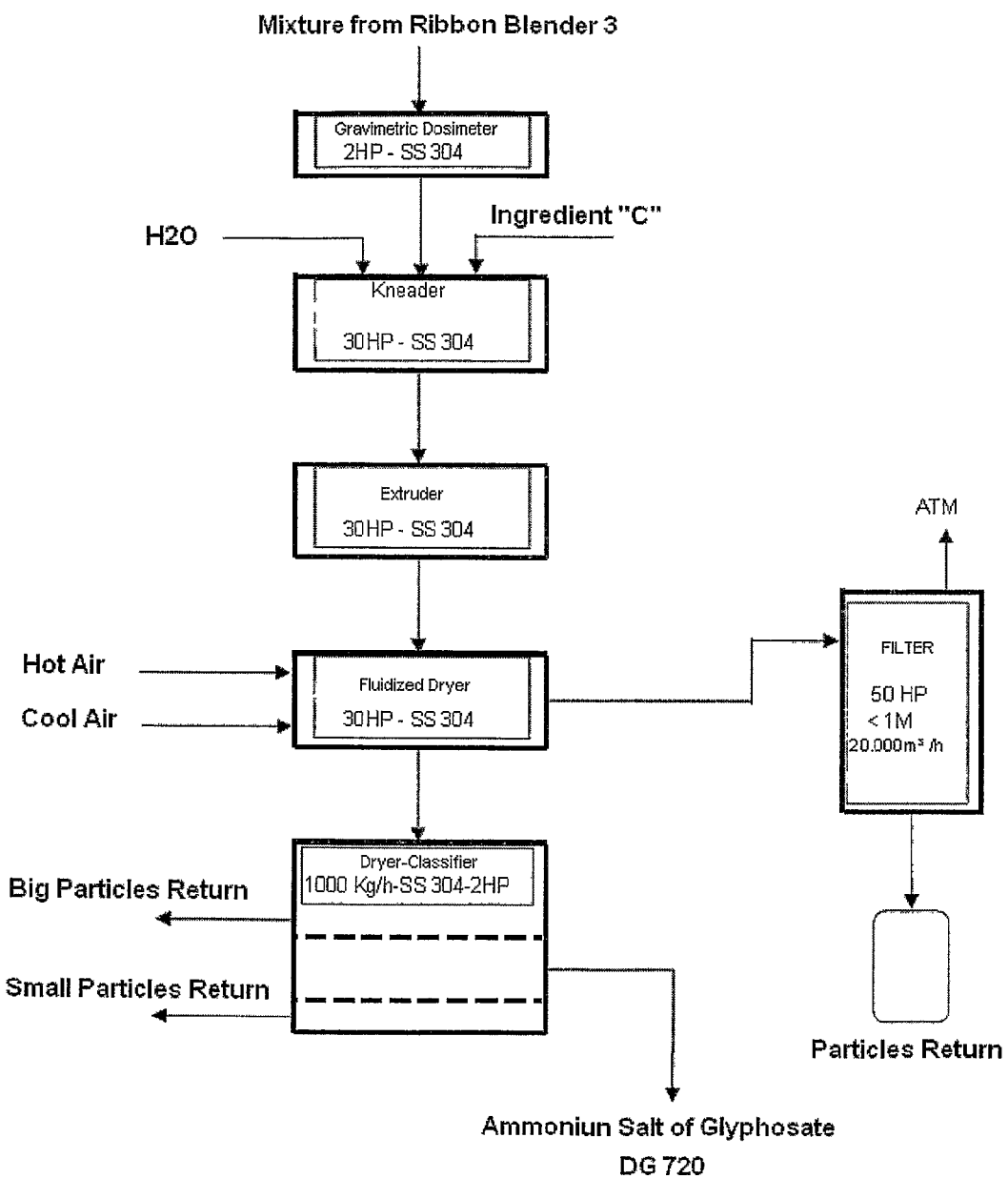
FIG. 4 shows a schematic diagram of another preferred embodiment of an industrial scale process for producing the solid, dry and water-soluble herbicide formulations in the form of dispersible granules (WDG) comprising the ammonium salt of glyphosate, where: the mixture leaving Ribbon Blender 3 shown in FIG. 2 is fed to a gravimetric dosimeter and then to a Kneader, to which water and an ingredient "C" are also fed; the material leaving the Kneader is fed to an extrusion equipment and then to Fluidized Dryer; the solid residues (powder and small granules) formed in the Fluidized Dryer are fed to a filter, so as said solid material is recycled; the dried dispersible granules (WDG) leave the Fluidized Dryer and feed a Dryer-Classifier; the extruded material which is not within the specifications is recycled; the extruded material which is within the specifications leave the Dryer-Classifier in the form of a WDG formulation with a concentration of 720 g/kg (in weight, based in the acid).

In yet another preferred embodiment of the invention, it is provided an industrial scale process for producing the solid, dry and water-soluble herbicide formulations in the form of dispersible granules (WDG) comprising the ammonium salt of glyphosate. Making reference to FIG. 4: the mixture leaving Ribbon Blender 3 shown in FIG. 2 is fed to a gravimetric dosimeter and then to a Kneader, to which water and an adjuvant (surfactant, preferably etoxylated fatty amines) are also fed; the material leaving the Kneader is fed to an extrusion equipment and then to Fluidized Dryer; the solid residues (powder and small granules) formed in the Fluidized Dryer are fed to a filter, so as said solid material is recycled; the dried dispersible granules (WDG) leave the Fluidized Dryer and feed a Dryer-Classifier; the extruded material which is not within the specifications is recycled; the extruded material which is within the specifications leave the Dryer-Classifier in the form of a WDG formulation with a concentration of 720 g/kg (% in weight, based in the acid).

The dry, solid herbicide formulations of the invention containing the "technical salt" of the invention may also comprise other active ingredients such as other herbicides, insecticides, fungicides, and combinations thereof. Those skilled in the art will readily appreciate from the teachings of the present invention that modifications on the preferred embodiments herein provided can be envisaged by combining other dry, solid adjuvants. Such alternative embodiments are to be deemed within the spirit of the invention and of the scope of the appended claims.

The invention claimed is:

1. A process for the preparation of solid salt of ammonium glyphosate characterized by comprising a solid/liquid/solid reaction, wherein a solid ammonium salt and a solid acid glyphosate are dispersed in a organic liquid and thereby react to form the solid salt of ammonium glyphosate.

2. The process according to claim 1, wherein said solid ammonium salt is selected from the group consisting of ammonium carbonate, ammonium hydrogen carbonate, and combinations thereof.

3. The process according to claim 1, wherein said organic liquid comprises at least one alcohol having up to four carbon atoms.

4. The process according to claim 1, wherein after the reaction is completed the product is separated from the organic liquid and is obtained as solid, water-soluble product having purity equal to or greater than 95% w/w.

5. The process according to claim 4, wherein said product is obtained as a solid, water-soluble product having humidity equal to or lower than 1% w/w.

6. The process according to claim 1, wherein the process is conducted at room temperature without substantial heat formation.

7. A solid and water-soluble active ingredient comprising an ammonium salt of glyphosate having purity equal to or greater than 95% w/w and a humidity equal to or lower than 1%.

8. The solid and water-soluble active ingredient according to claim 7, wherein said ammonium salt is selected from group consisting of ammonium carbonate, ammonium hydrogen carbonate, and combinations thereof.

9. A solid and water-soluble herbicide formulation, comprising:
at least one ammonium salt of glyphosate having purity equal to or greater than 95% w/w; and
at least one dry, solid adjuvant.

10. The solid and water-soluble herbicide formulation according to claim 9, wherein said adjuvant is an etoxylated fatty alcohol.

11. The solid and water-soluble herbicide formulation according to claim 10, wherein said etoxylated fatty alcohol has 16 to 18 carbon atoms.

12. The solid and water-soluble herbicide formulation according to claim 9, wherein said ammonium salt is the monoammonium salt of glyphosate.

13. A process for the preparation of a solid, water-soluble herbicide formulation, comprising mixing:
at least one ammonium salt of glyphosate having purity equal to or greater than 95% w/w; and
at least one dry, solid adjuvant.

14. The process according to claim 13, wherein said solid ammonium salt is the monoammonium salt of glyphosate.

15. A process for controlling weeds comprising the application, to the plant culture to be protected, of an agrochemical comprising as active ingredient the ammonium salt of glyphosate having purity equal to or greater than 95% w/w.

16. A method for preparing an agrochemical for controlling weeds, comprising adding to the agrochemical an active ingredient comprising the ammonium salt of glyphosate having purity equal to or greater than 95% w/w.

17. The process as claimed in claim 3, wherein said organic liquid further comprises other alcohols and/or other organic solvents.

* * * * *